United States Patent
Jain et al.

(10) Patent No.: US 10,610,196 B2
(45) Date of Patent: Apr. 7, 2020

(54) SHAPE INJECTION INTO ULTRASOUND IMAGE TO CALIBRATE BEAM PATTERNS IN REAL-TIME

(71) Applicant: KONINKLIJKE PHILIPS N.V., Eindhoven (NL)

(72) Inventors: Ameet Kumar Jain, New York, NY (US); Francois Guy Gerard Marie Vignon, Hudson, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1135 days.

(21) Appl. No.: 14/898,648

(22) PCT Filed: Jun. 30, 2014

(86) PCT No.: PCT/IB2014/062714
§ 371 (c)(1),
(2) Date: Dec. 15, 2015

(87) PCT Pub. No.: WO2014/207728
PCT Pub. Date: Dec. 31, 2014

(65) Prior Publication Data
US 2016/0128668 A1    May 12, 2016

Related U.S. Application Data

(60) Provisional application No. 61/840,503, filed on Jun. 28, 2013.

(51) Int. Cl.
*A61B 8/00* (2006.01)
*A61B 8/08* (2006.01)
(Continued)

(52) U.S. Cl.
CPC ............ *A61B 8/0841* (2013.01); *A61B 8/585* (2013.01); *G01S 7/52073* (2013.01); *G01S 15/74* (2013.01);
(Continued)

(58) Field of Classification Search
CPC .................................................. A61B 8/0841
See application file for complete search history.

(56) References Cited

U.S. PATENT DOCUMENTS

| 4,249,539 A | 2/1981 | Vilkomerson et al. |
| 4,407,294 A | 10/1983 | Vilkomerson |

(Continued)

FOREIGN PATENT DOCUMENTS

| WO | 9216148 A1 | 10/1992 |
| WO | 2005055849 A1 | 6/2005 |

(Continued)

OTHER PUBLICATIONS

Breyer B., et al., "Ultrasonically Marked Catheter—A Method for Positive Echographic Catheter Position Identification", Medical and Biological Engineering and Computing, Springer, Heildelberg, DE, vol. 22, No. 3, May 1, 1984, pp. 268-271.

(Continued)

*Primary Examiner* — Joseph M Santos Rodriguez

(57) ABSTRACT

A probe (122) transmits and receives ultrasonic energy to and from a volume and a marker device (120) configured to respond to a received ultrasonic signal and emit an ultrasonic signal after a delay. The ultrasonic signal includes one or more pulses configured to generate a marker, when rendered, of a given size at a position within an image. A medical instrument (102) is disposed in the volume and includes the marker device. A control module (124) is stored in memory and is configured to interpret the ultrasonic energy received from the probe and from the marker device (Continued)

to determine a three dimensional location of the medical instrument and to highlight the three dimensional location of the marker device with the marker in the image.

12 Claims, 6 Drawing Sheets

(51) Int. Cl.
  *G01S 15/89* (2006.01)
  *G01S 7/52* (2006.01)
  *G01S 15/74* (2006.01)
  *A61B 90/00* (2016.01)
  *A61B 34/20* (2016.01)

(52) U.S. Cl.
  CPC ............... *G01S 15/899* (2013.01); *A61B 8/08* (2013.01); *A61B 8/463* (2013.01); *A61B 2034/2063* (2016.02); *A61B 2090/3925* (2016.02); *A61B 2090/3929* (2016.02)

(56) References Cited

U.S. PATENT DOCUMENTS

| | | |
|---|---|---|
| 5,158,088 A | 10/1992 | Nelson et al. |
| 5,161,536 A | 11/1992 | Vilkomerson et al. |
| 5,779,638 A | 7/1998 | Vesely et al. |
| 5,921,930 A | 7/1999 | Uberle |
| 6,592,526 B1 | 7/2003 | Lenker |
| 8,200,313 B1 | 6/2012 | Rambod et al. |
| 2003/0060700 A1 | 3/2003 | Solf et al. |
| 2013/0041252 A1 | 2/2013 | Vignon et al. |
| 2013/0116538 A1 | 5/2013 | Herzog et al. |

FOREIGN PATENT DOCUMENTS

| | | |
|---|---|---|
| WO | 2011138698 A1 | 11/2011 |
| WO | 2012024201 A1 | 2/2012 |
| WO | 2012066437 A1 | 5/2012 |
| WO | 2013001437 A1 | 1/2013 |
| WO | 2014207728 A1 | 12/2014 |

OTHER PUBLICATIONS

Merdes, et al., "Locating a Catheter Transducer in a Three-Dimensional Ultrasound Imaging Field", IEEE Transactions on Biomedical Engineering, vol. 48, No. 12, Dec. 2001, pp. 1444-1452.

Nikolov, et al., "Precision of Needle Tip Localization Using a Receiver in the Needle", 2008 IEEE International Ultrasonics Symposium Proceedings, Digital Object Identifier: 10.1109/ULTSYM.2008.0117, pp. 479-482.

Mung, et al., "A non-disruptive technology for robust 3D tool tracking for ultrasound-guided interventions." Medical Image Computing and Computer-Assisted Intervention—MICCAI 2011. Springer Berlin Heidelberg, 2011. pp. 153-160.

Vilkomerson, "A system for ultrasonic beacon-guidance of catheters and other minimally-invasive medical devices" IEEE TUFCC 44(2), pp. 496-504.

SHAPE INJECTION INTO ULTRASOUND IMAGE TO CALIBRATE BEAM PATTERNS IN REAL-TIME

CROSS-REFERENCE TO PRIOR APPLICATIONS

This application is the U.S. National Phase application under 35 U.S.C. § 371 of International Application No. PCT/IB2014/062714, filed on Jun. 30, 2014, which claims the benefit of U.S. Provisional Patent Application No. 61/840,503, filed on Jun. 28, 2013. These applications are hereby incorporated by reference herein.

BACKGROUND

Technical Field

This disclosure relates to medical instruments and more particularly to a system and method for highlighting instruments in images with special shapes using acoustics.

Description of the Related Art

Needles, catheters and other interventional tools are often difficult to visualize under ultrasound due to their specular nature and unfavorable incidence angles. One solution for marking a needle tip under ultrasound guidance is to embed a small ultrasound sensor at the tip of the needle. Such a sensor receives the direct ultrasound signals that impinge upon it as imaging beams from an ultrasound imaging probe sweep the field of view. Different ways of using these signals to highlight the position of the transducer in the ultrasound image have been proposed. These ways rely on time-of-flight of ultrasound from the imaging probe to the sensor for estimating the range coordinate of the sensor, and on the intensity of the received signals as the imaging beams sweep the field of view to recover the lateral coordinate. To estimate time of flight, one must have access to the line trigger events of the scanner, and to estimate the lateral coordinates, one must have access to the frame trigger event and to the coordinates and steering angles of the imaging beams.

SUMMARY

In accordance with the present principles, a system for highlighting an instrument in an image includes a probe for transmitting and receiving ultrasonic energy to and from a volume and a marker device configured to respond to a received ultrasonic signal and emit an ultrasonic signal after a delay. The ultrasonic signal includes one or more pulses configured to generate a marker, when rendered, of a given size at a position within an image. A medical instrument is disposed in the volume and includes the marker device. A control module is stored in memory and is configured to interpret the ultrasonic energy received from the probe and from the marker device to determine a three dimensional location of the medical instrument and to highlight the three dimensional location of the marker device with the marker in the image.

Another system for injecting a shape in an image includes a probe for transmitting and receiving ultrasonic energy to and from a volume and a marker device configured to respond to a received ultrasonic signal and emit an ultrasonic signal after a delay. The ultrasonic signal includes one or more pulses configured to generate a marker, when rendered, of a given size at a position within an image. A medical instrument is disposed in the volume and includes the marker device. A workstation includes a processor and memory. The memory stores a control module configured to interpret the ultrasonic energy received from the probe and from the marker device to determine a three dimensional location of the medical instrument and to highlight the three dimensional location of the marker device with the marker in the image and an image processing module configured to compare a position and shape of the injected signal to an on-screen video output of a position and shape of the marker to determine beamforming parameters.

A method for providing a shaped marker in an image includes estimating a frame rate of an imaging probe; analyzing traces within a detection window to find a temporal maximum which best matches a position of a marker device mounted on an instrument to determine an arrival time; injecting an acoustic feedback signal into the imaging probe by emitting a delayed signal from the marker device to the imaging probe, the delayed signal including one or more timed pulses to simulate a marker shape in an echo back from the marker device; and displaying the marker shape in an image to identify the position of the instrument.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
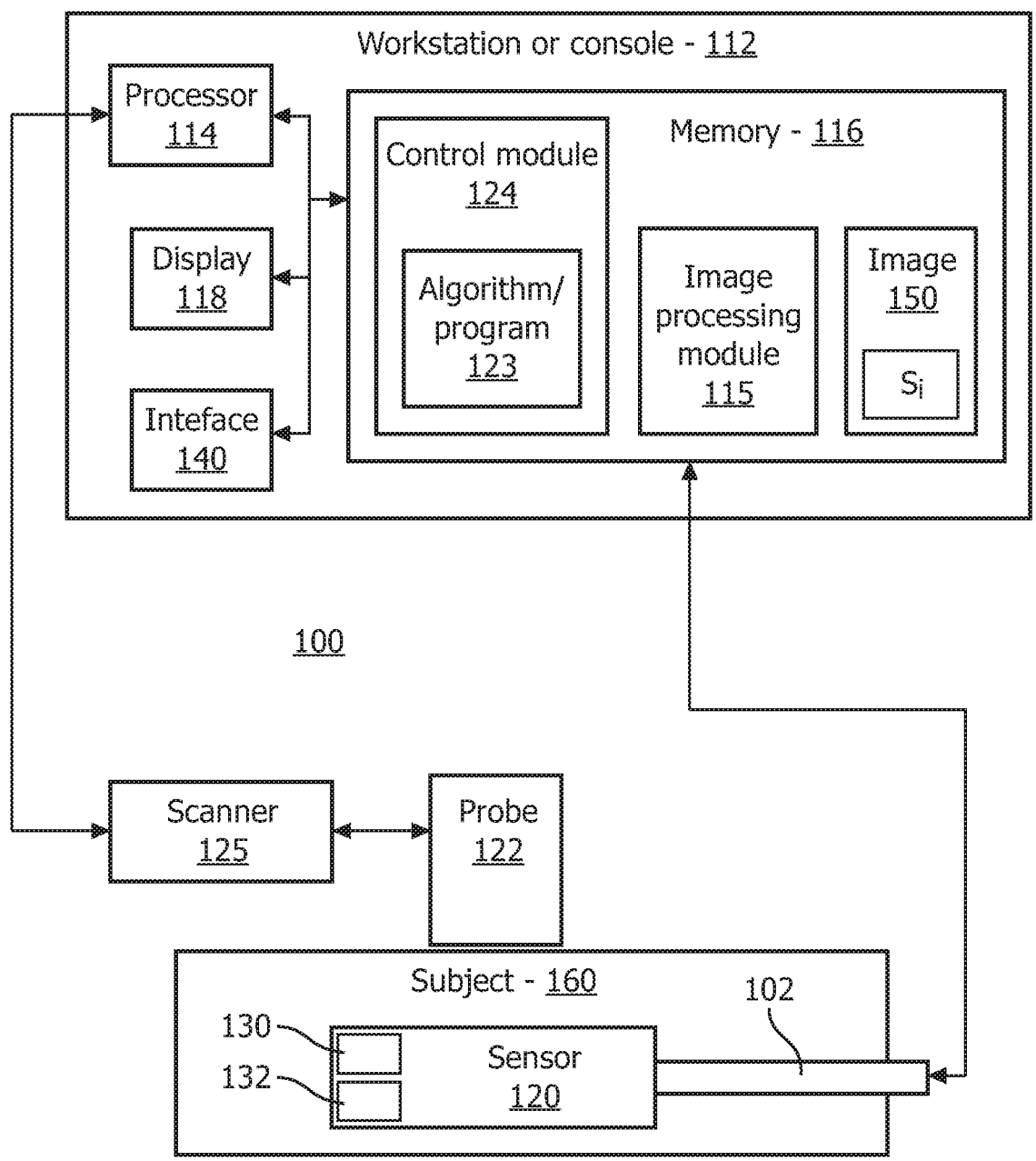
FIG. 1 is a block/flow diagram showing a system for providing a shaped, acoustically rendered marker in an ultrasound image in accordance with one embodiment.

In accordance with the present principles, systems and methods permit highlighting of a position of a sensor using special shapes and/or effects. A sensor or sensors are employed on a medical device (e.g., an interventional device) to 'inject' an acoustic signal at a right time inside an ultrasound (US) image. This injected acoustic signal will be perceived by the scanner as a response to its own acoustic field. The signal is processed by a scanner's beamforming pipeline and ultimately, visualized on the US image. Note that even though we may not know the time when the acoustic waves were transmitted by the scanner, the acoustic waves will nevertheless create a signal on the sensor, which is exploited for highlighting the sensor. When the device is inserted inside the US region, a one-time calibration step is run to estimate a frame rate (T) of the imaging mode being used. Second, a temporal maximum ($t_0$) of the signals received by the sensor is found, with respect to an arbitrary origin. Third, the sensor is switched to a transmit mode, and an impulse is emitted from it at a time $t_1=t_0+nT+S_i$, n being an integer and $S_i$ providing pulses (times) to generate a desired shape or shapes. That impulse propagates toward an imaging probe and a subsequent signal is beamformed by the scanner machine. A final visual display shows an echo coming from the sensor location and having the desired shape or shapes.

Piezoelectric sensors are employed to inject special temporal acoustic signals inside the tissue. Since the US scanner will perceive this signal to be part of its own 'reflected' acoustic wave, it will place this signal inside the US image. Note that due to transmission and absorption losses of the original acoustic wave of the scanner, the injected signal will have, e.g., a greater than 30 dB signal advantage over the reflected signal from tissue. More notably, special temporal patterns are provided during signal injection. These patterns will result in planned special shapes in the US image. Injected shapes could include concentric circles, ellipses, arrows, lines, curves, crosses, three dimensional objects, etc. of any shape, size and position in the image, as desired by the automatic injection system. Note that this shape can be injected 'permanently' in the image so that a user can see it all the time, or injected just instantaneously in one single US frame, making it practically invisible to the user. These shapes or markers are provided to mark a tool position or may be employed to be offset to indicate or track other useful positions in real-time. The present embodiments describe 2D images (e.g., right and left beams, and 2D shapes); however the 2D arrays, images and shapes may be extended and include 3D arrays, images and shapes.

Additionally, since most US scanners also provide a video-out, the video-out signal, together with the injected signal, can be analyzed to quantitatively estimate the internal beam-forming and scan conversion parameters. Since the approximate position and shape of the injected signal is known, a priori, an automated algorithm can pick the exact position and size of the shape from the US image (a function of the internal parameters). This position and shape can then be compared to the estimated injected shape. An optimization routine can then estimate the internal beam-forming and scan conversion parameters. Based on the current parameters, a new shape can now be injected. This process can be performed sequentially in a closed-loop manner, by injecting and detecting an updated shape of varying size/position. For example, the shape could start with an ellipse and end with two concentric circles as the parameters become known. Parameters that can be automatically estimated include beam-angles, absolute beam firing times, left beam number, right beam, depth, etc. This complete self-calibration process could be shown to the user or be kept 'invisible'.

The present principles permit less reliance on the availability of particular scanner data for pinpointing the position of an instrument. For example, a frame, line triggers and beamforming parameters are no longer needed from the scanner. This allows ultrasound-equipped tools to be self-contained (no need for low-level interfacing with the scanner) thus allowing them to be usable with a broad installed base of ultrasound machines from any vendor. In one embodiment, the system is capable of on-the-fly reverse-engineering of crucial parameters from the imaging scanner, e.g., frame rate and line trigger positions, analog acoustic signal injection into the scanner's receive signal path, etc.

It should be understood that the present invention will be described in terms of needles; however, the teachings of the present invention are much broader and are applicable to any medical instruments or other instruments tracked by acoustic energy. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements. The present embodiments may be employed any time an instrument is inserted into the body under ultrasound guidance, this includes needle procedures (biopsies, ablation, anesthesia, pain management, abscess drainage, etc.), catheter procedures (heart repair, electrophysiology, etc.) or any other procedures.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Referring now to the drawings in which like numerals represent the same or similar elements and initially to FIG. 1, a system 100 is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store an image processing module 115 configured to process signals from an ultrasonic scanner 125. Module 115 is configured to use the US signals to reconstruct structures deformations, deflections and other changes associated with a medical device, instrument or tool 102 and/or its surrounding region. The medical instrument 102 may include a needle, a catheter, a guidewire, a probe, an endoscope, a robot, an electrode, a filter device, a balloon device, or other medical component, etc.

An acoustic sensor (including a transmitter or transponder) 120 is mounted on the medical instrument 102 to be highlighted. A probe 122, such as a US probe 122 is provided for scanning a patient or subject 160. The probe 122 is capable of reception (to sense signal emission by the probe 122). The received signals at the probe 122 are coupled to a simple data-analysis and control module 124 stored in memory 116 and capable of some amount of signal processing in algorithm/program 123 (e.g., Fast Fourier Transform (FFT), max identification, optional curve fitting, etc.). It should be understood that the control module 124 and the image processing module 115 may be combined in a single component or provided separately, as indicated.

In particularly useful embodiments, the ultrasound sensor 120 is placed at the tip of a needle (for example). That sensor 120 senses ultrasound signals as beams from the imaging probe 122 as it sweeps the field of view. The US signals are analyzed by the workstation 112 and/or in the control module 124 to extract a frame repetition period T, and a time of arrival $t_0$ of a maximum signal at the sensor 120. One or more frames later, the sensor 120 is switched into a transmit mode and emits a pulse that includes shape effects $S_i$ (at, e.g., $t_0+T+S_i$ or $t_0+nT+S_i$, where n is an integer). The scanner 125 interprets the pulse as being a high echo coming from a position of the sensor 120, thus highlighting the sensor 120 and, in turn, the instrument 102 on an image 150 even under slight out-of-plane alignment.

In particularly useful embodiments, the ultrasound sensor or marker device 120 includes a receive function 130 and a transmit function 132. The ultrasound sensor 120 may include a receiver/transmitter pair, a transponder or a transducer with a transmitter/receiver (T/R) switch on the interventional tool or instrument 102 to be highlighted. A transponder is a device that emits an identifying signal in response to an interrogating received signal. The signal received at the receiver function 130 of the sensor 120, while the imaging probe 122 emits ultrasound into the medium, is coupled to the data-analysis control module 124 capable of signal processing (FFT, max identification, optionally curve fitting) and slow switches. The transmit function 132 is provided for acoustic signal injection back into the medium (to the probe 122 to be processed in the control module 124). In one example, the sensor 120 aboard the tool 102 includes a transponder (which is also used in a transmit mode). This may call for higher voltage circuits (in the tens of volts) and need to reasonably match the frequencies of the imaging probe 122 and that of the transponder (the signal from the transponder need not be filtered out in the scanner's receive signal path). The transponder may also include a transmit/receive (T/R) switch to switch between a receive mode and transmit mode. In another example, an additional ultrasound emitter for the transmit function 132 may be placed on the device close to the receiver function 130 (or co-located as a transceiver so that received and transmitted signals have a common location). This eliminates the need for a T/R switch and simplifies the detection/injection software.

A display 118 shows a location of the sensor and includes the shapes or visual effects of the injected signal ($S_i$). Display 118 may also permit a user to interact with the workstation 112 and its components and functions, or any other element within the system 100. This is further facilitated by an interface 140 which may include a keyboard, mouse, a joystick, a haptic device, or any other peripheral or control to permit user feedback from and interaction with the workstation 112.

In another embodiment, a video signal-out from the scanner 125 and the instrument 102 with the sensor 120 are employed to compute a 3D location of the instrument 102 at any given time. The video-out signal is easily available on commercial scanners and is streamed into the computational workstation 112.

When the sensor 120 is switched to transmit mode and an impulse is emitted therefrom, the impulse propagates toward the imaging probe 122 and the subsequent signal is beam-formed by the scanner 125. A final display provides an echo coming from the sensor location. For example, one or more frames later, when the sensor 120 is switched into transmit mode, a series of pulses may be emitted at times ($t_0+T+S_i$), where $S_i$ determines a shape observed/marked on the US image.

Figure 2:
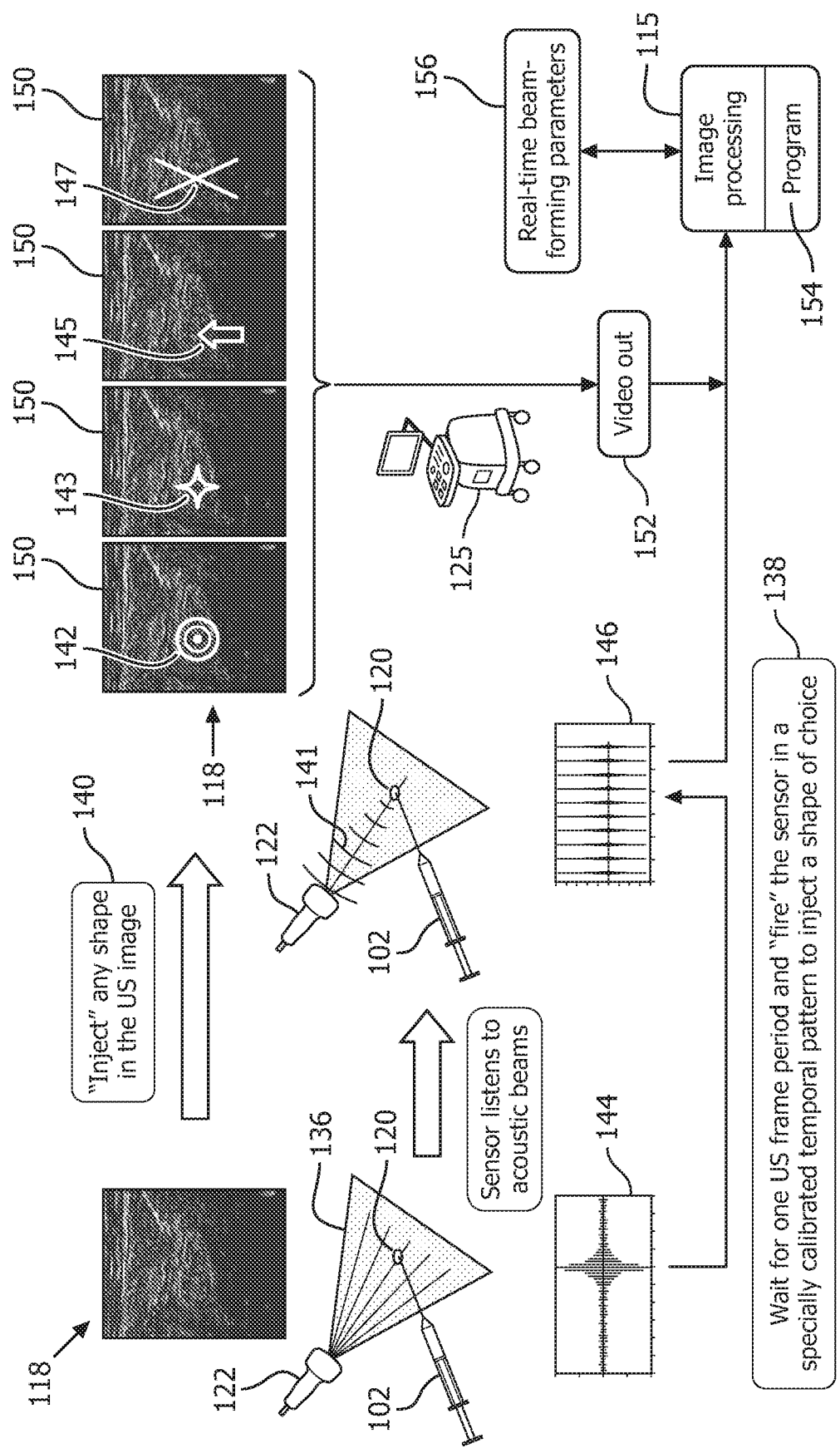
FIG. 2 is a conceptual diagram showing a system for providing the shaped, acoustically rendered marker in accordance with one embodiment.

Referring to FIG. 2, a conceptual diagram shows interaction between components in accordance with one illustrative embodiment. Signal injection is performed with the sensor 120 with a timed or responsive US emission. The sensor 120 is placed at the tip of the device 102 to be highlighted. Example signals 136 received by that sensor/transponder 120 during one imaging frame from the probe 122 are shown. The sensor 120 senses ultrasound signals 136 as beams from the imaging probe 122 sweep. The signals 136 are analyzed to extract the frame repetition period T, and the time of arrival $t_0$ of the maximum signal at the sensor 120. One or two (or more) frames later (138), the sensor 120 is switched into transmit mode and emits a pulse (at, e.g., $t_0+T+S_i$ or $t_0+nT+S_i$). The scanner 125 interprets the pulse or pulses as being a high echo coming from the position of the sensor 120, thus highlighting it on an image 150.

The system 100 identifies the position of the maximum and its timing relative to the line trigger information from plots 144 and 146. One (or more) frame period(s) 138 later, a signal 141 is injected by the sensor/transponder 120 back to the probe 122 with the appropriate timing to generate a bright marker or markers 142, 143, 145, 147 where the sensor 120 is located and is visible on the display 118. Illustrative markers 142, 143, 145, 147 are depicted with unique shapes. Marker 142 includes concentric circles about a pinpointed position of the sensor 120. Marker 143 includes a star-like shape centered on the pinpointed position of the sensor 120. Marker 145 includes an arrow shape pointing to the pinpointed position of the sensor 120. Marker 147 includes an "X" shape pointing to the pinpointed position of the sensor 120.

In particularly useful embodiments, if $S_i$ is fixed to just a single fire or pulse firing and set to 0, then the marker seen on the image will just be a dot. In other examples, if $S_i$ is set to $-2t_0$, $-1t_0$, $0$, $t_0$, $2t_0$, then the response will be a small line segment roughly parallel to the horizontal axis. In sector and curved probe geometries, the curvature of this line segment will allow on-the-fly identification of the beamforming and scan conversion parameters. Note that for a linear scanner, increasing the number of fires at periodic time slots will create a long horizontal line. If $S_i$ is set to $-k(t_0+x)$ where k goes from $-K$ to $+K$, a slanted straight line is created on a linear probe where the slope depends on x and the length of the segment depends on K. By controlling x and observing the response on the image, the beam-forming and scan conversion parameters can be estimated. $S_i$ can similarly be set to a variety of functions to get a variety of shapes such as circles, ellipses, stars, etc.

Note that this shape or marker can be injected 'permanently' in the image 150 so that a user can see it all the time, or injected just instantaneously in one single US frame, making it practically invisible to the user. Additionally, since most US scanners also provide a video-out 152, the video-out signal can be analyzed, together with the injected signal, to quantitatively estimate the internal beam-forming and scan conversion parameters in the image processor or processing module 115.

In one embodiment, the image processing module 115 compares the approximate position and shape of the injected signal 141, which is known, a priori, to the video out image 152 using an automated algorithm or program 154, configured to determine an exact position and size of the shape (e.g., marker 142, 143, 145, 147) from the US image 150. This can be as a function of the internal display parameters or pixel assignments, etc. The position and shape is compared to the estimated injected shape. An optimization routine 156 can then estimate the internal beam-forming and scan conversion parameters. This comparison may be employed as a check on position or may be employed for other functions. For example, based on the current estimate of the internal parameters, a new shape can now be injected at a same or different position. Note that this process can be done sequentially in a closed-loop manner, by injecting and detecting an updated shape of varying size/position. This can be employed to impose blinking effects, alternating size increased/decreases, spinning or translating shapes, etc.

In one example, the shape (e.g., marker 142, 143, 145, 147) could start with an ellipse and end with two concentric circles as the parameters become known. Parameters that can be automatically estimated may include beam-angles, absolute beam firing times, left beam number, right beam number, depth, etc. This complete self-calibration process may be shown to the user or be kept 'invisible'.

Figure 3:
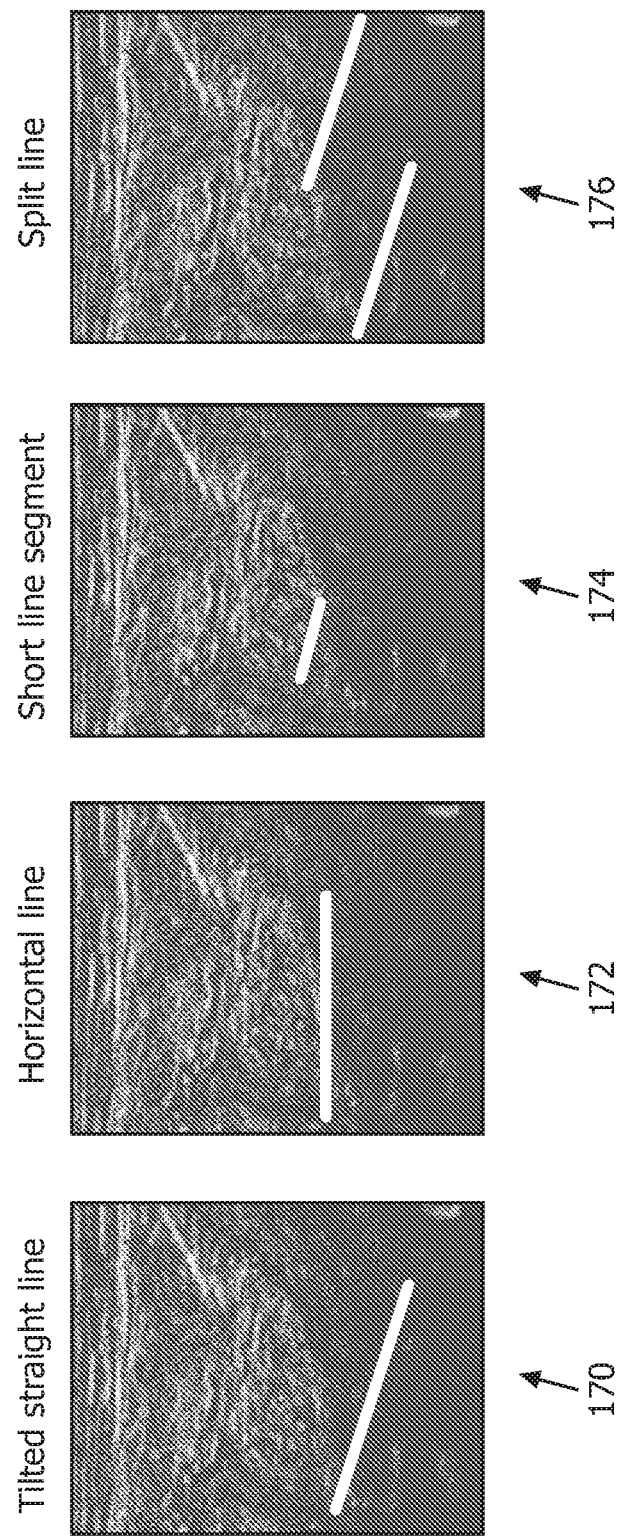
FIG. 3 is a diagram showing images having shaped, acoustically rendered markers shown in accordance with other embodiments.

Referring to FIG. 3, four images (150) are shown with different linear shapes generated therein. One image 170 shows a tilted straight line shape. Another image 172 shows a horizontal line shape. Another image 174 shows a short line segment shape, and another image 176 shows a split line shape. A straight line can be used as a calibration shape since straight lines are simple and accurate for automatic segmentation. Different lines could be drawn and picked up in the image. As an example, to identify the 'beginning' beam, a split line (176) can be very useful. In addition, the system could 'flash' one shape, do some analysis, and then flash a second frame, and so on until all the needed parameters are identified. Within a few frames (e.g., <1 sec.), all parameters should be available. Given that the beamforming parameters are dynamic, but not changing in real-time, this routine could be run in the background using the image processing module 115 every few seconds to check if the parameters have changed. Alternately, the calibration routine could be triggered every time a significant change is observed in a frame-grabbed video out from the scanner 125.

Figure 4:
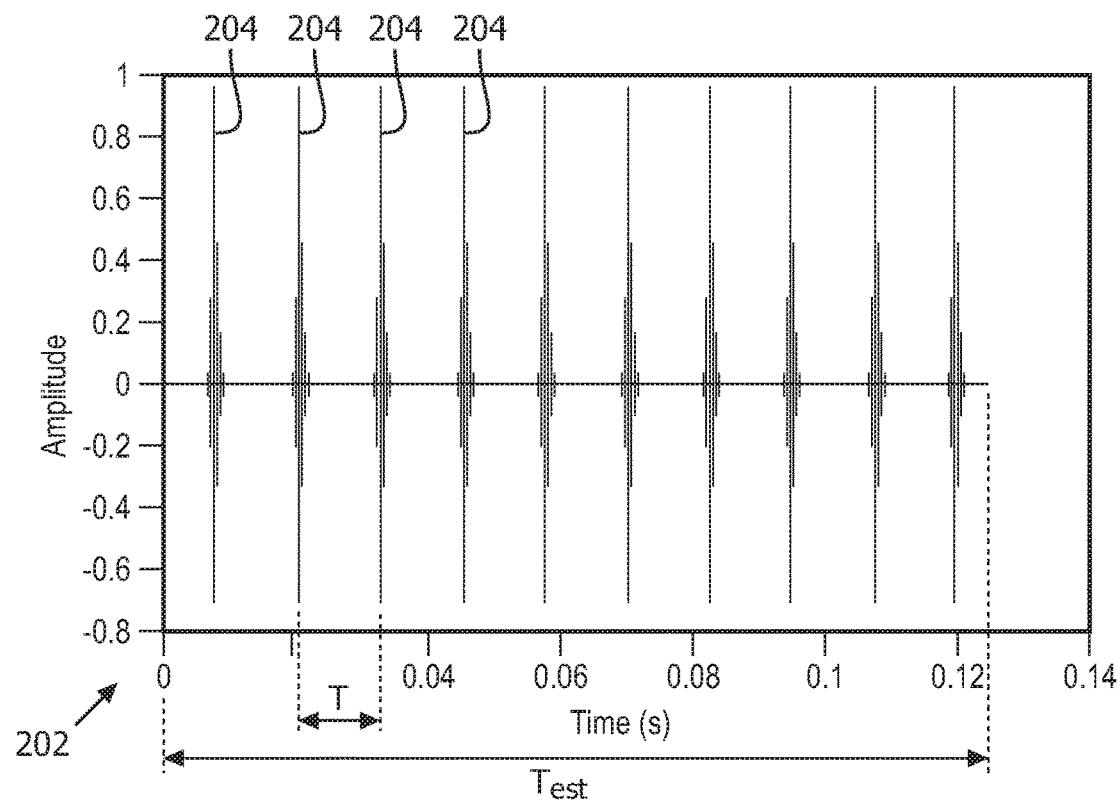
FIG. 4 is a plot of amplitude versus time showing ultrasound pulses for estimating frame rate in accordance with one embodiment.

Referring to FIG. 4, a frame rate T of the imaging probe needs to be estimated. This is done by listening to a received signal for a relatively long time $T_{est}$ (e.g., a quarter of a second, to record, e.g., 10 frames at 40 Hz) and analyzing the signal for its dominant period, i.e., by Fourier analysis. A received trace 202 is depicted in FIG. 4. On the trace 202, individual impulses 204 correspond to different beams hitting the sensor (120 on the device 102) (the amplitude varies as beams get closer and then further from the sensor 120). The pattern is then repeated several times as several identical frames are acquired in continuous sequence. The trace 202 received by the sensor (120) during a time $T_{est}$ can be used to estimate the frame rate T of the system. Once this is done, the receiver system analyzes traces of a length $T_{detect}$ ($T < T_{detect} < 2T$, ideally).

Figure 5:
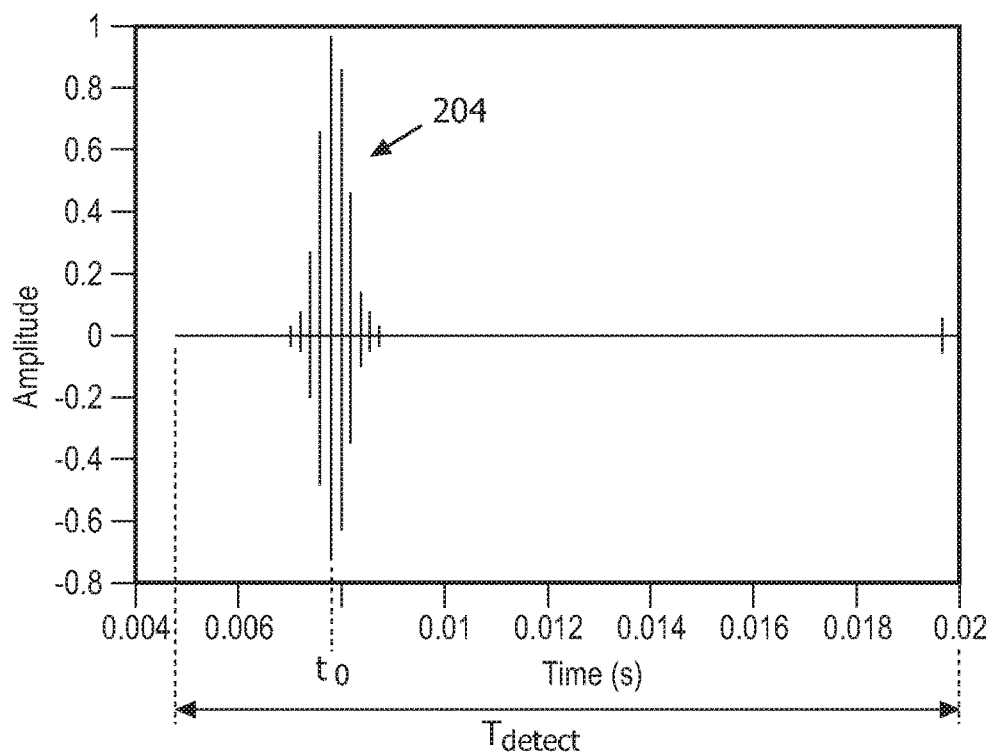
FIG. 5 is a plot of amplitude versus time showing an ultrasound pulse for determining a detection time in accordance with one embodiment.

Referring to FIG. 5, one of these impulses 204 of a length $T_{detect}$ is depicted. Note that acquisition of these impulses 204 is not synchronized with the frames. The system searches for the temporal maximum $t_0$ of this trace. That maximum corresponds to the instant when the pulse from the transmit event that is best aligned with the sensor 120 reaches the sensor 120. The trace received by the sensor 120 during a time $T_{detect}$ (e.g., $T_{detect}=1.2T$ here) is used to find the time $t_0$ when the most on-axis transmit reaches the sensor 120. $t_0$ is simply the temporal maximum of the impulse or trace 204.

Instead of a simple peak detection for identifying the beam closest to the sensor 120 and the arrival time, it may be advantageous to fit the curve or trace 204 (e.g., signals received by the sensor 120 during $T_{est}$) to the local maxima of the individual pulses or to a simple signal model, e.g., a polynomial or a Gaussian.

Next, an acoustic signal is injected back into the imaging probe 122 to create an echo that comes from the sensor position. It may also be desirable for the injected acoustic signal to blink (short periods of "injection on" alternating with periods of "injection off"). The human eye is more sensitive to a blinking signal. In other embodiments, visual effects may be imparted to the acoustic echo to change its size, change its shape or change its visual attributes as described. These visual effects may be introduced through the signal generated or sent back from the sensor 120. If the videostream is captured and synchronized to the signal acquisition and injection setup, differential images can be generated to highlight the injected signal (the "blink off" image is subtracted from the "blink on" image). The differential images can be enhanced and superimposed on the original image in an entirely image-processing chain that only requires access to video data from the scanner 125.

Figure 6:
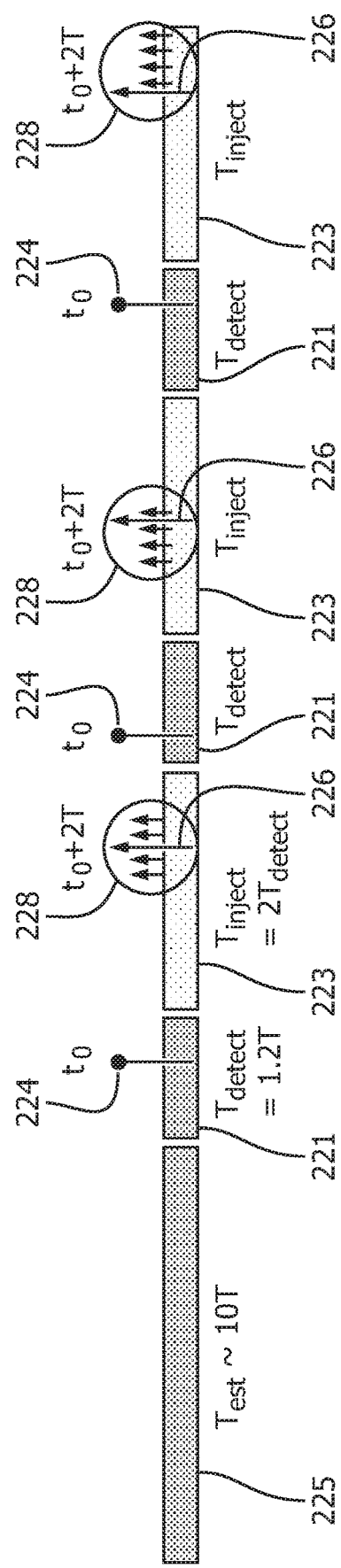
FIG. 6 is an event time line showing events occurring between a marker device of an instrument/tool and a probe in accordance with one embodiment.

For FIG. 6, two embodiments may illustratively be described: the sensor 120 is a transponder (can be switched into a transmit mode with a T/R switch), or two transducers in close proximity are used, one being a receiver for signal detection and the other one being a transmitter for signal injection. Either way, the sequence of events outlined in FIG. 6 applies.

Referring to FIG. 6, a sequence of events for frame rate estimation, peak pulse detection, and pulse injection in the transponder embodiment are illustratively shown. Note that the external system's clock may be totally independent from the US scanner's clock. A relatively long period 225 ($T_{est}$) (long enough to comfortably span tens of frames) is used to estimate the imaging system's frame rate. Then, peak detection periods 221 (receive mode, darker shade) alternate with signal injection periods 223 (transmit mode, lighter shade). If a signal peak is detected at a time $t_0$, a signal is injected at $t_0+2T$; this creates an artificial echo at the position of the transponder two frames after its detection. Detection events 224 are depicted as rounded ends, and injection events 226 are arrows.

After detection, an impulse is sent from the transponder or transmitter at a time $t_0+nT+S_i$, where $S_i$ determines the shape observed/marked on the US image and n being an integer, preferably n=1 (transmitter embodiment) or 2 (transponder embodiment). Shape pulses 228 are depicted in circles at injection events 226. This has the effect of creating an artificial echo or echos that seems to come from the sensor position or other position, n frames after the detection frame. The trace analysis and injection of a feedback signal may be repeated to actualize the position of the sensor 120. Frame rate estimation may also be repeated periodically to account for possible parameter changes as the user changes the imaging settings (imaging mode, settings, and depth may all affect frame rate).

Next, in one embodiment, the injected video is frame-grabbed and an automated segmentation algorithm is employed to determine a location and shape of the shape inside the US image. This provides a real-time estimate of the beamforming and scan conversion parameters as described above. Note that the parameters may need adjustment if estimated by using a single image. Hence, an embodiment may iterate through the process steps using minor (or major) changes in the injected shape to maximize the accuracy of the parameter estimation. Note that these shapes could be flashed in split-second times so that a pattern will be practically invisible to a user. Post-calibration, the patterns could be entirely stopped, or replaced by patterns that only highlight the shape of the entire/partial device, or replaced by periodic flashes to recheck the calibration. The calibration can be done periodically in the background, or when a significant change is perceived in the frame-grabbed image from the video out.

In accordance with the present principles, the embodiments described herein may be employed any time an instrument is inserted into a body under ultrasound guidance. This includes needle procedures (biopsies, ablation, anesthesia, pain management, abscess drainage, etc.) and catheter procedures (heart repair, electrophysiology, etc.), and others.

Figure 7:
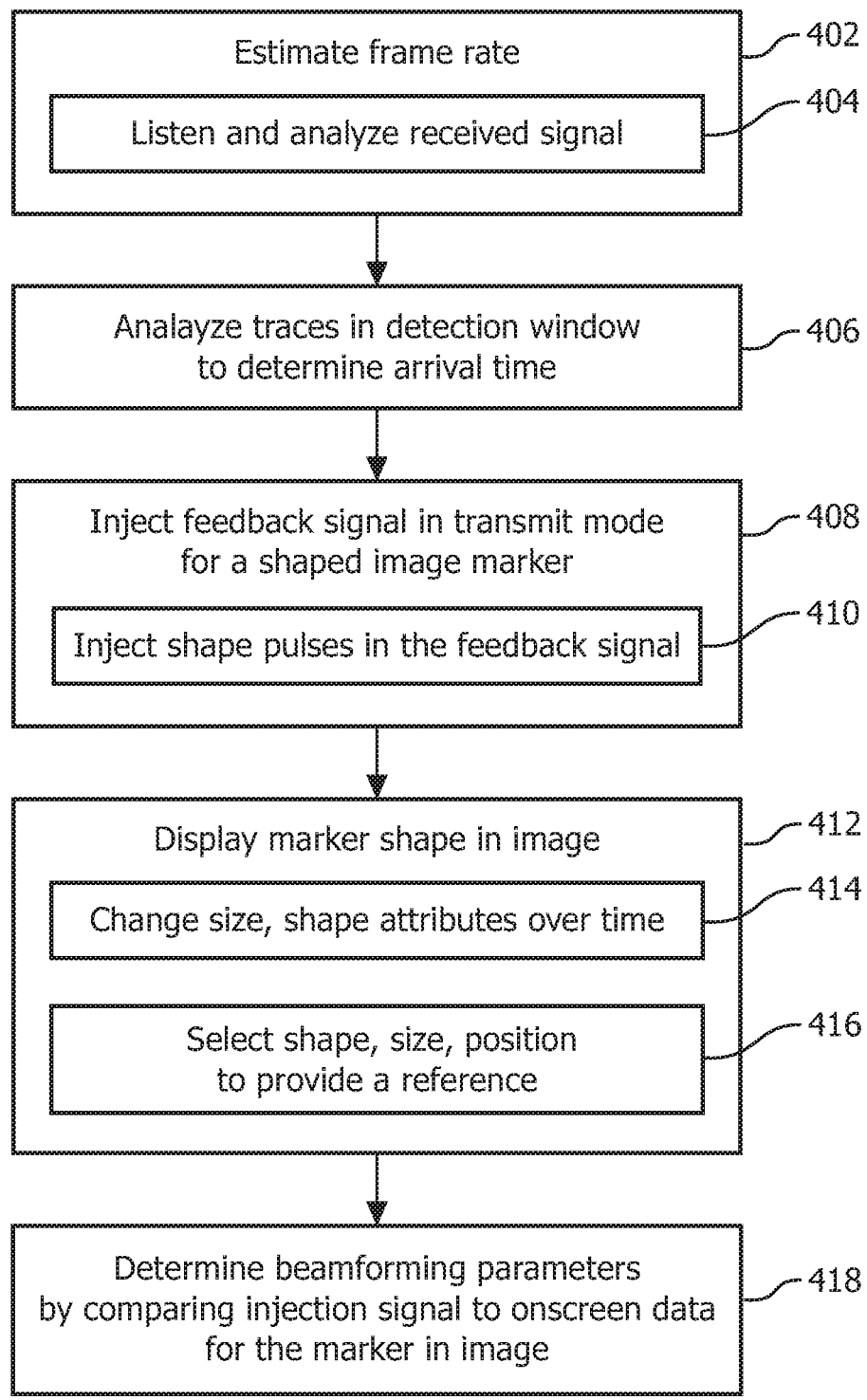
FIG. 7 is a flow diagram showing a method for providing a shaped acoustically rendered marker in an ultrasound image in accordance with one illustrative embodiment.

Referring to FIG. 7, a method for providing a shaped marker in an image is shown in accordance with one embodiment. In block 402, a frame rate of an imaging probe is estimated. In block 404, estimating the frame rate may include listening to a received signal for a period of time, and analyzing the received signal to determine its dominant period.

In block 406, traces are analyzed to determine if they are within a detection window to find a temporal maximum which best matches a position of a sensor or marker device mounted on an instrument to determine an arrival time. The detection window includes a detection time $T_{detect}$ between T and 2T, where T is the frame rate.

In block 408, an acoustic feedback signal is injected into the imaging probe by emitting a delayed signal from the marker device to the imaging probe. The delayed signal includes one or more timed pulses to simulate a marker shape in an echo back from the marker device. The injected signal is generated by a transponder or transceiver (transmitter) on the instrument to the imaging probe to simulate an echo back from the sensor mounted on the instrument. In block 410, the acoustic feedback signal may be injected in frames at $t_0+nT+S_i$, where $t_0$ is a temporal maximum of signals received by the sensor, T is frame rate, n is an integer and $S_i$ includes shape pulses.

In block 412, the marker shape is displayed in an image to identify the position of the instrument. In block 414, displaying the marker shape may include changing one of shape, size and visual attributes of the marker over time. In block 416, displaying the marker shape may include selecting a shape, size and position of the marker to provide a reference. The reference may be employed for indicating a position of the instrument in use (e.g., during tracking), aligning other instruments, making measurements, delineating organs or any other use.

In block 418, a position and shape of the delayed signal may be compared to an on-screen video output of a position and shape of the marker to determine beamforming parameters of a scanner. Once the beamforming parameters of the scanner are determined, the marker and other images or overlays may be placed or rendered in the images.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for acoustic highlighting of interventional instruments (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for injecting a shape in an image of an ultrasonic scanner, comprising:
an ultrasonic scanner configured to generate an image and a video-out signal;
a probe connected to the ultrasound scanner and configured to transmit and receive ultrasonic signals to and from a volume;
a marker device configured to respond to the ultrasonic signal by emitting an ultrasonic signal to the probe after a delay, the ultrasonic signal emitted by the marker device including one or more pulses configured to generate a marker, to be rendered, of a given size at a position within the image, the marker device further being configured to emit the ultrasonic signal delay at times $t_0+n_T+S_i$ where $t_0$ is a temporal maximum of signals received by the marker device, T is a frame repetition period of the imaging mode executed by the ultrasound scanner, n is an integer, and $S_i$ corresponds to one of a plurality of selectable shapes of the marker;
a medical instrument configured to be disposed in the volume and including the marker device; and a control processor configured to:
  interpret the ultrasonic energy received by the probe from the marker device to determine a three dimensional location of the medical instrument,
  reconstruct the ultrasonic energy received from the volume into the image,
  highlight the three dimensional location of the marker device with the marker in the image,
  extract the frame repetition period T of the imaging mode executed by the ultrasound scanner, and
  from the video-out signal from the ultrasound scanner and the ultrasonic signal emitted by the marker device, qualitatively estimate internal beam forming and scan conversion parameters of the ultrasound scanner.

2. The system as recited in claim 1, wherein the marker device includes a transponder and the transponder includes a switch, the switch being configured to change the marker device from a receive mode to a transmit mode.

3. The system as recited in claim 1, wherein the marker device includes a transceiver having a receiver and a transmitter.

4. The system as recited in claim 1, wherein the control processor is further configured to compare a location of the marker device in the image with a location of the marker device derived from the video-out signal.

5. The system as recited in claim 1, wherein the control processor is further configured to change the shape of the marker to another one of the selectable shapes of the marker.

6. The system as recited in claim 1, wherein the marker changes at least one of the shape, size and visual attributes over time.

7. The system as recited in claim 1, wherein the marker is configured to indicate a position of the marker device.

8. The system as recited in claim 1, wherein the marker is configured to indicate a reference position.

9. A system injecting a marker icon of a preselected shape in an ultrasound image of a volume of interest of a subject, the system comprising:
  a medical instrument configured to be disposed in the volume of interest;
  an ultrasound probe configured to transmit ultrasound signals into the volume of interest and receive ultrasound signals from the volume of interest, the received signals including ultrasound echo signals indicative of locations of anatomical structures and the medical instrument in the volume of interest;
  a marker transponder attached to the medical instrument and configured to receive the ultrasound signals transmitted by the ultrasound probe and transmit ultrasound marker signals to the ultrasound probe delay period after receiving the ultrasound signals transmitted by the probe, the delay period being an integer multiple of an ultrasound frame repetition period T of an imaging mode executed by the ultrasound probe plus a delay and number of marker transducer firings in a calibrated temporal pattern $S_i$ to inject a marker icon of a selected pattern and a time $t_0$ of arrival of a maximum ultrasound signal transmitted from the ultrasound probe;
  a display device configured to display the ultrasound image and the marker icon; and
  one or more computer processors configured to:
    reconstruct the ultrasound image from the ultrasound signals received from the ultrasound probe, the ultrasound image depicting the locations of the anatomical structures and the medical instrument,
    determine a location of the marker transponder and the selected patterns for the marker icon from the ultrasound marker signals received by the ultrasound probe, and
  control the display device to display the ultrasound image with the marker icon of the selected pattern at the location of the marker transponder.

10. The system as recited in claim 9, wherein the marker transponder is further configured to output an electrical signal to the one or more processors indicative of the ultrasonic signals transmitted by the ultrasound during an ultrasound scan of the volume of interest and wherein the one or more processors are further configured to:
  determine the frame repetition period T at the time of arrival $t_0$ from the electrical signal.

11. The system as recited in claim 10, further including:
  a user interface configured to receive a user selection of another pattern for the marker icon and control the marker transducer to generate a temporal firing pattern indicative of the selected another pattern.

12. A system for providing a shaped marker in an image of an ultrasound scanner configured to generate a video-out signal, the system comprising:
  a marker device mounted on an instrument configured to receive an ultrasonic signal transmitted by an imaging probe of the ultrasound scanner and output an electrical signal based on the received ultrasonic signal;
  means for estimating, from the electronic signal, a frame repetition period T of an imaging mode used by the imaging probe;
  means for analyzing the received ultrasonic signal within a detection window to find a time of arrival to of a maximum signal from the imaging probe by the marker device which best matches a position of the marker device;
  means for injecting an acoustic feedback signal to the imaging probe by emitting a delayed ultrasonic signal from the marker device to the imaging probe, the delayed ultrasonic signal including one or more timed pulses $S_i$ to simulate a marker icon shape;
  means for displaying the marker icon shape in the image to identify a position of the instrument;
  wherein the means for injecting the acoustic feedback signal includes injecting the acoustic feedback signal in frames at $t_0+n_T+S_i$, where n is an integer and T is a time delay corresponding to the emission of one or more pulses which, when rendered in the image, corresponds to the marker shape; and
  means for analyzing the video-out signal of the ultrasound scanner together with the injected signal to quantitatively estimate internal beam forming and scan conversion parameters of the ultrasound scanner.

* * * * *